United States Patent [19]

Baker et al.

[11] Patent Number: 5,731,266
[45] Date of Patent: Mar. 24, 1998

[54] HERBICIDAL COMPOSITIONS COMPRISING DIAMINO-1,3,5-TRIAZINE AND CHLOROACETANILIDE HERBICIDES AND A SURFACTANT SYSTEM

[75] Inventors: Larry I. Baker, Greensboro; Michael J. Hopkinson, Pleasant Garden, both of N.C.

[73] Assignee: Ciba-Geigy Corporation, Tarrytown, N.Y.

[21] Appl. No.: 228,911

[22] Filed: Apr. 18, 1994

Related U.S. Application Data

[63] Continuation of Ser. No. 32,941, Mar. 17, 1993, abandoned.

[51] Int. Cl.$^6$ .................. A01N 43/70; A01N 37/22; A01N 25/30
[52] U.S. Cl. .................................................. 504/133
[58] Field of Search ........................................ 504/133

[56] References Cited

U.S. PATENT DOCUMENTS

| | | | |
|---|---|---|---|
| 2,891,855 | 6/1959 | Gysin et al. | 71/2.5 |
| 3,937,730 | 2/1976 | Vogel et al. | 71/118 |
| 4,022,611 | 5/1977 | Vogel et al. | 71/118 |
| 4,168,965 | 9/1979 | Vogel et al. | 71/118 |
| 4,200,451 | 4/1980 | Vogel et al. | 71/118 |
| 4,305,750 | 12/1981 | Kleuser et al. | 71/92 |
| 4,324,580 | 4/1982 | Vogel et al. | 71/118 |
| 4,371,390 | 2/1983 | LeClair et al. | 71/93 |
| 4,372,777 | 2/1983 | LeClair et al. | 71/93 |
| 4,411,692 | 10/1983 | LeClair et al. | 71/93 |
| 4,411,693 | 10/1983 | LeClair et al. | 71/DIG. 1 |
| 4,461,641 | 7/1984 | Abildt et al. | 71/DIG. 1 |
| 4,594,096 | 6/1986 | Albrecht et al. | 71/93 |
| 4,663,364 | 5/1987 | Iwasaki et al. | 523/122 |
| 4,678,503 | 7/1987 | Barlet et al. | 71/93 |
| 4,770,694 | 9/1988 | Iwasaki et al. | 71/93 |
| 4,804,399 | 2/1989 | Albrecht et al. | 71/93 |
| 4,824,475 | 4/1989 | Marbley et al. | 71/DIG. 1 |
| 4,851,421 | 7/1989 | Iwasaki et al. | 514/352 |
| 4,875,929 | 10/1989 | Morgan et al. | 71/121 |
| 4,936,901 | 6/1990 | Surgant, Sr. et al. | 504/133 |
| 5,019,150 | 5/1991 | Martin et al. | 71/90 |
| 5,121,083 | 6/1992 | Bauer et al. | 330/295 |

*Primary Examiner*—José G. Dees
*Attorney, Agent, or Firm*—Marla J. Mathias

[57] ABSTRACT

Flowable herbicidal compositions which contain an active component combination of at least one triazine and at least one chloroacetanilide with a surfactant component. This surfactant component, which consists of an anionic compound based on a monosulfuric acid ester of alkyl or alkyphenol polyglycol ethers as well as at least one nonionic alkyl or alkylphenol polyglycol ether, gives stable dispersions of the concentrated composition and forms stable dispersions of dilutions of the compositions suitable for direct use.

3 Claims, No Drawings

HERBICIDAL COMPOSITIONS COMPRISING DIAMINO-1,3,5-TRIAZINE AND CHLOROACETANILIDE HERBICIDES AND A SURFACTANT SYSTEM

This is a continuation of Ser. No. 032,941, filed Mar. 17, 1993, abandoned.

The present invention relates to a flowable herbicidal composition in the form of an aqueous dispersion which contains an active ingredient mixture comprising at least one triazine and at least one chloroacetanilide and a novel mixture of surfactants, triazines and chloroacetanilides, processes for their production and their action as herbicides are known from U.S. Pat. No. 2,891,855 and German Offenlegungsschrift No. 2,328,340. Mixtures of these two classes of compound are commercially available in the form of aqueous dispersions. The combinations of active ingredient contained therein differ in the concentration of the individual compounds according to the crop, the nature of the application, climate and the regional weed population.

Each of these active ingredient combinations of triazines and chloroacetanilides specially adjusted to the particular requirements needs a particular formulation, i.e. especially a different kind of combination of surfactants. The formulation of such active ingredient combinations is further complicated by the fact that the different crystal forms of the same active ingredient that may result from different preparatory, methods necessitate another formulation, while otherwise retaining the same ratio of active ingredients to one another. The consequence is that numerous different formulations of the combination of the same active ingredients are necessary and this entails both for the producer and for the end user a considerable risk regarding the safety of applying these compositions. Hence there exists a need to provide a mode of formulation which permits all changes conditional on biological and technological factors in the active ingredient concentration of a flowable concentrated dispersion, without it being necessary to compound the surfactant content of the formulation completely anew. Such a formulation is described in U.S. Pat. No. 4,461,641.

In addition, there exists a need to ensure that these compositions give stable dispersions on dilution under the many varying conditions of commercial use.

Accordingly, the present invention has for its object to formulate a flowable herbicidal composition comprising at least one solid disperse phase and a continuous aqueous phase and containing, as active component, a combination of at least one triazine and at least one chloroanilide, such that said composition contains 10 to 50% by weight of at least one triazine of the formula I

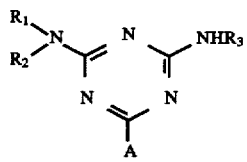

wherein A is chlorine, methoxy or methylthio, $R_1$ is $C_1$–$C_4$alkyl, $R_2$ hydrogen or $C_1$–$C_4$alkyl, and $R_3$ is $C_1$–$C_4$cycloalkyl, $C_1$–$C_5$alkyl or $C_1$–$C_4$alkyl substituted by methoxy or cyano, or a mixture thereof;

10 to 50% by weight of at least one chloroacetanilide of the formula II

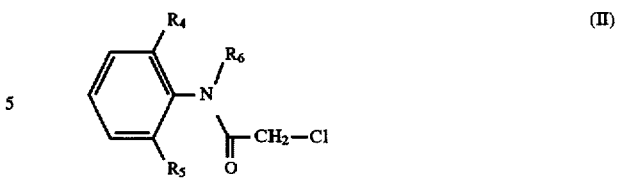

wherein $R_4$ and $R_5$, independently of each other, are methyl or ethyl, and $R_6$ is $C_3$–$C_4$alkynyl, $C_1$–$C_3$alkyl or $C_1$–$C_3$alkyl substituted by $C_1$–$C_4$alkoxy, ethoxycarbonyl or pyrazolyl, or a mixture thereof;

1 to 10% by weight of at least one anionic surfactant of the formula III

wherein B is $C_{12}$–$C_{18}$alkyl and x averages 3, or B is $C_9$alkylphenyl and x averages 4, $M^\oplus$ is an ammonium, sodium, potassium, diethanolammonium or triethanolammonium cation, or a protonated cationic form of the formula IV

wherein $R_7$ is $C_8$–$C_{18}$alkyl, $C_8$–$C_{18}$alkadienoyl or $C_8$–$C_{18}$alkatrienoyl, and m and n together average from about 2 to 60;

0.5 10% by weight of at least one non-ionic polyglycol ether surfactant of the formula V

wherein p is an integer from 2 to 90, q is an integer from 0 to 60, and $R_8$ is $C_4C_{18}$alkyl, $C_{10}$–$C_{22}$alkenoyl, $C_{12}$–$C_{22}$alkatrienoyl or phenyl which is substitute; and water.

The composition may also contain 0 to 5% by weight of a thickener which is soluble or able to swell in water, and 0 to 25% by weight of a frost protective agent.

In the definitions of the radicals $R_1$ to $R_6$, alkyl is methyl, ethyl, n-propyl, isopropyl and the butyl isomers. Alkoxy is e.g. methoxy, ethoxy, n-propoxy, isopropoxy and the butoxy isomers. Alkenyl is propargyl, 2-butynyl, 3-butynyl and methylpropargyl. Cycloalkyl radicals are cyclopropyl and cyclobutyl.

Examples of compounds (active ingredients) which can be formulated in the compositions of the invention are:

2-chloro-4,6-bis(ethylamino)-1,3,5-triazine (simazine), 2-chloro-4-ethylamino-6-isopropylamino-1,3,5-triazine (atrazine), 2-(4-chloro-6-ethylamino-1,3,5-triazine-2-ylamino)-2-methylpropionitrile (cyanazine), 2-chloro-4-cyclopropylamino-6-isopropylamino-1,3,5-triazine (cyprazine), 2-tert-butylamino-4-chloro-6-ethylamino-1,3,5-triazine (terbutylazine), 2-chloro-4,6-bix(isopropylamino)1,3,5-triazine (propazine), 2-chloro-4-isopropylamino-6-(3-methoxypropylamino)-1,3,5-triazine (mesoprazine), 2-chloro-4-tert-butylamino-1,3,5-triazine, 2-chloro-4-ethylamino-6-diethylamino-1,3,5-triazine, 2-chloro-4-ethylamino-6-sec-butylamino-1,3,5-triazine, as well as α-chloro-2'-ethyl-6'-methyl-N-(ethoxymethyl)-acetanilide (acetochlor), 2-chloro-N-(2-methoxyethyl)acet-2',6'-xylidide (dimethachlor), 2-chloro-6'-ethyl-N-(2-methoxy-1-methylethyl)acet-o-toluidide (metolachlor), 2-chloro-2',6'-diethyl-N-(methoxymethyl)acetanilide (alachlor), N-(butoxymethyl)-2-chloro-2',6'-diethylacetanilide (butachlor), α-chloro-2'-ethyl-6'-methyl-N-(propargyl)acetanilide, α-chloro-2'-ethyl-6'-methyl-N-(pyrazol-1-ylmethyl)acetanilide (metazolachlor), and 2-chloro-2',6'-diethyl-N-(2-propoxyethyl)acetanilide (pretilachlor).

Among the triazine compounds, those compounds are preferred which carry only secondary amino groups as substituents, e.g.

2-chloro-4,6-bis(ethylamino)-1,3,5-triazine, 2-chloro-4-ethylamino-6-isopropylamino-1,3,5-triazine, 2-(4-chloro-6-ethylamino-1,3,5-triazin-2-yl-amino)-2-methylpropionitrile, 2-tert-butylamino-4-chloro-6-ethylamino-1,3,5-triazine and 2-chloro-4-cyclopropylamino-6-isopropylamino-1,3,5-triazine Among the acetanilides, those compounds are preferred which carry an alkoxyalkyl group of altogether at most 5 carbon atoms at the nitrogen atom, e.g.

α-chloro-2'-ethyl-6'-methyl-N-(ethoxymethyl)acetanilide, 2-chloro-N-(2-methoxyethyl)acet-2',6'-xylidide, 2-chloro-6'-ethyl-N-(2-methoxy-1-methylethyl)acet-o-toluidide, 2-chloro-2',6'-diethyl-N-(methoxymethyl)acetanilide, N-butoxymethyl-2-chloro-2',6'-diethylacetanilide, and 2-chloro-2',6'-diethyl-N-(2propoxyethyl)acetanilide.

Examples of substituted phenyl groups in the definitions of $R_8$ are 4-nonylphenyl, 2,4,6-tributylphenyl, 2,4,6-tristyrylphenyl, 2,4-dinonylphenyl, 2,4,6-tripentylphenyl, 2,4-distyrylphenyl, 4-styrylphenyl, 2,3,4,6-tetrabutylphenyl, 4-decylphenyl, 4-heptylphenyl, 4-pentylphenyl, 2,4-dihexylphenyl, 2,4-dioctylphenyl, 4-octylphenyl, 4-hexylphenyl, 2,4-dipentylphenyl, 2,4,6-tripentylphenyl, 4-cyclohexylphenyl, 4-cyclopentylphenyl and 2,4-dicyclohexylphenyl.

Alkyl radicals of 12 to 22 carbon atoms comprise linear radicals such as n-dodecyl, n-tridecyl, n-tetradecyl, n-pentadecyl, n-hexadecyl, n-hexadecyl, n-heptadecyl and n-octadecyl, and also the isomers thereof with branches chains, e.g. trimethylnonyl, tetramethylnonyl, dimethylundecyl and dipropylhexyl.

Alkanoyl, alkenoyl, alkadienoyl or alkatrienoyl radicals as understood in the definition of $R_8$ are the carboxylic acid radicals which are derived e.g. from the following saturated carboxylic acids: lauric acid ($C_{12}$), myristic acid ($C_{14}$), pentadecylic acid ($C_{15}$), palmitic acid ($C_{16}$) margaric acid ($C_{17}$), stearic acid ($C_{18}$), arachidic acid ($C_{20}$),behenic acid ($C_{22}$) or tuberculostearic acid ($C_{19}$), or from the following simply unsaturated carboxylic acids: lauroleic acid ($C_{12}$), myristoleic acid ($C_{14}$), palmitoleic acid ($C_{16}$), pertroselinic acid ($C_{18}$), oleic acid ($C_{18}$), elaidic acid ($C_{18}$), vaccenic acid ($C_{18}$) or erucic acid ($C_{22}$), or from the following carboxylic acids having double to triple unsaturation: linolic acid ($C_{18}$), linolenic acid ($C_{18}$), ricinenic acid ($C_{18}$) and α-eleaostearic acid ($C_{18}$).

In order to adjust an optimum degree of viscosity it is frequently necessary to add to the herbicidal composition a thickener which is soluble or able to swell in water. Such suitable thickeners are: polysaccharides of the xantham, alignate, guar or cellulose type, or synthetic macromolecules such as polyethylene glycols, polyvinyl pyrrolidones, polyvinyl alcohols, polyacrylates of swellable structure-forming silicates such as pyrogenic or precipitated silicic acids, bentonites, mommorillonites, hectonites, attapulgites or organic derivatives of the cited structures of aluminium silicates.

In order to maintain the flow properties of the herbicidal composition at low temperatures and to prevent the homogeneous aqueous phase from freezing, frost protectives are normally added to the compositions of the invention. Conventional additives such as ethylene glycol, propylene glycol, glycerol, diethylene glycol, triethylene glycol and tetraethylene glycol and urea are suitable for this purpose.

The formulations contain in general 10 to 50% by weight of a herbicidal triazine of the formula I or of a mixture of such compounds. Commercial compositions preferably contain 15 to 35% by weight of triazine. The content of herbicidal chloroacetanilide, or mixture of chloroacetanilides, is also 10 to 50% by weight, preferably 10 to 40 % by weight. The combination also contains 1 to 10% by weight of an anionic surfactant of formula III, and 0.5 to 10% by weight of at least one nonionic surfactant of the formula V. The flowable herbicidal compositions of the invention optionally contain 0 to 5% by weight of a thickener and 0 to 25% by weight of a frost protective.

The composition of the invention has excellent tolerance to changes in the identity of the active ingredients, required for optimum biological effects, and to changes in the quality of the active ingredients, required from technical manufacturing considerations. The surfactant systems described give formulations with excellent storage stability characteristics.

The particular advantage of the composition of the invention relates to its behavior at the user level. For a typical use, the composition is diluted with water and/or liquid fertilizes and sprayed on fields or agricultural crops. For dilution in liquid fertilizers, typically a concentrated aqueous solution of urea and ammonium nitrate, it is essential to have an anionic surfactants in order to obtain a stable dispersion. The water used for the dilutions may come from a well, surface water such as a pond, or a municipal water system. These waters may range form pH 5 to pH 9. Dilution of the composition of the invention with water also shows the same pH range. The anionic parts of the surfactant systems previously used for similar compositions are based on weak acids such as partially esterified phosphoric acid or carboxylic acids. These have $pK_a$'s in the pH range described above. This means that during use the anionic parts of the surfactant system can change from protonated to non-protonated forms and vice versa. This chemical change alters the surfactant properties leading to a variation in performance of the composition dependent on the pH of the water used for dilution.

In the composition of the present invention, the anionic part of the surfactant system is formed from a partially esterified strong acid. The $pK_a$ is outside of the pH range of dilutions for use. The performance of this composition is thus independent of the water used for dilution.

Preferred compositions of the invention comprise the following constituents:

20 to 50% by weight of water, 15 to 35% by weight of a triazine of the formula I or of a mixture of two such compounds, 10 to 40% by weight of a chloroacetanilide of the formula II, 1 to 10% by weight of an anionic surfactant of the formula III, and 0.5 to 10% by weight of at least one nonionic surfactant of the formula V.

In a typical manufacturing procedure, the triazine, or mixture of triazines, is mixed with the water, glycol, and one or more of the nonionic surfactants. The average particle size of this dispersion should be between 3 and 10 microns which can be accomplished by dry grinding the triazines prior to dispersion or by wet grinding the dispersion. The thickening agent and preservative are than added to the dispersion and given sufficient time to dissolve or disperse. The anionic surfactant is added to the chloroacetanilide to form a dispersion or solution. The two parts of the formulation are then blended together to give the final composition.

The following are examples of compositions manufactured according to the above process. The following examples are for illustrative purposes only and are not in any way intended to limit the scope of the claims presented hereinafter.

EXAMPLE 1

| | |
|---|---|
| 30.00% | by weight of atrazine, |
| 36.50% | by weight of metolachlor, |
| 3.90% | by weight of an alkoxylated nonylphenol sulfate, containing an average of 4 ethylene oxide units and neutralized with an alkoxylated tallowamine containing an average of 5 ethylene oxide units, |
| 1.90% | by weight of nonylphenol alkoxylated with an average of 20 propylene oxide units and 30 ethylene oxide units, |
| 2.00% | by weight of an alkoxylated $C_{13}$alcohol containing an average of 6 ethylene oxide units, |
| 3.50% | by weight of ethylene glycol as a frost protective agent, |
| 0.05% | by weight of a polysaccharide as a thickening agent, |
| 0.02% | by weight of formaldehyde as a preservative for the thickening agent, and |
| — | water to make up 100%. |

EXAMPLE 2

| | |
|---|---|
| 18.30% | by weight of atrazine, |
| 36.60% | by weight of metolachlor, |
| 3.90% | by weight of an ammonium salt of an alkoxylated nonylphenol sulfate, containing an average of 4 ethylene oxide units, |
| 1.90% | by weight of butyl alcohol alkoxylated with an average of 30 propylene oxide units and 30 ethylene oxide units, |
| 2.00% | by weight of an alkoxylated $C_{14}$alcohol containing an average of 6 ethylene oxide units, |
| 3.90% | by weight of ethylene glycol as a frost protective agent, |
| 0.10% | by weight of a polysaccharide as a thickening agent, |
| 0.05% | by weight of formaldehyde as a preservative for the thickening agent, and |
| — | water to make up 100%. |

EXAMPLE 3

| | |
|---|---|
| 22.00% | by weight of cyanazine, |
| 22.00% | by weight of metolachlor, |
| 3.20% | by weight of an alkoxylated nonylphenol sulfate, containing an average of 4 ethylene oxide units and neutralized with an alkoxylated tallowamine containing an average of 8 ethylene oxide units, |
| 2.20% | by weight of nonylphenol alkoxylated with an average of 30 propylene oxide units and 30 ethylene oxide units, |
| 1.80% | by weight of an alkoxylated $C_{19}$alcohol containing an average of 5 ethylene oxide units, |
| 5.00% | by weight of ethylene glycol as a frost protective agent, |
| 0.12% | by weight of a polysaccharide as a thickening agent, |
| 0.06% | by weight of formaldehyde as a preservative for the thickening agent, and |
| — | water to make up 100%. |

EXAMPLE 4

| | |
|---|---|
| 11.00% | by weight of atrazine, |
| 11.00% | by weight of cyanazine, |
| 22.00% | by weight of metolachlor, |
| 4.20% | by weight of a sodium salt of an alkoxylated nonylphenol sulfate, containing an average of 4 ethylene oxide units, |
| 1.90% | by weight of nonylphenol alkoxylated with an average of 30 propylene oxide units and 40 ethylene oxide units, |
| 1.20% | by weight of an alkoxylated $C_{13}$alcohol containing an average of 6 ethylene oxide units, |
| 1.00% | by weight of an alkoxylated nonyl phenol with an average of 9 ethylene oxide units, |
| 5.00% | by weight of ethylene glycol as a frost protective agent, |
| 0.15% | by weight of a polysaccharide as a thickening agent, |
| 0.07% | by weight of formaldehyde as a preservative for the thickening agent, and |
| — | water to make up 100%. |

It will thus be seen that the objects set forth above, among those made apparent from the preceding description, are efficiently attained and, since certain changes may be made in carrying out the above composition and in the method set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What we claim is:

1. A flowable herbicidal composition having at least one solid disperse phase and a continuous aqueous phase comprising
   (a) combination of
      (i) 10 to 50% by weight of at least one triazine of the formula I

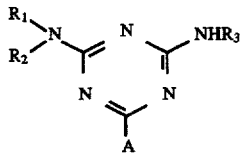

wherein

A is chlorine, $R_1$ is $C_1$–$C_4$alkyl, $R_2$ hydrogen or $C_1$–$C_4$alkyl, and $R_3$ is $C_1$–$C_4$cycloalkyl, $C_1$–$C_5$alkyl or $C_1$–$C_4$alkyl substituted by methoxy or cyano, or a mixture thereof; and (ii) 10 to 50% by weight of at least one chloroacetanilide of the formula II

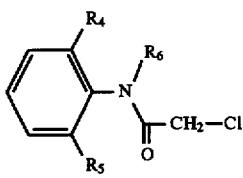

(II)

wherein $R_4$ and $R_5$, independently of each other, are methyl or ethyl, and $R_6$ is $C_3$-$C_4$alkynyl, $C_1$-$C_3$alkyl or $C_1$-$C_3$alkyl substituted by $C_1$-$C_4$alkoxy, or a mixture thereof; and (b) a surfactant system consisting of
1 to 10% by weight of at least one anionic surfactant of the formula III

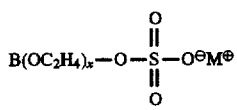

(III)

wherein

B is $C_{12}$-$C_{18}$alkyl and x averages about 3, or B is $C_9$alkylphenyl and x averages about 4, $M^\oplus$ is an ammonium, sodium, potassium, diethanolammonium or triethanolammonium cation, or a protonated cationic form of the formula IV

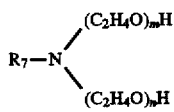

(IV)

wherein $R_7'$ is $C_8$-$C_{18}$alkyl, $C_8$-$C_{18}$alkadienoyl or $C_8$-$C_{18}$alkatrienoyl, and m and n together average from about 2 to 60; and
(ii) 0.5 to 10% by weight of at least one non-ionic polyglycol ether surfactant of the formula V

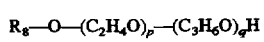

(V)

wherein p is an integer from about 2 to 90, q is an integer form about 0 to 60, and $R_8$ is $C_4$-$C_{18}$alkyl, $C_{10}$-$C_{22}$alkenoyl, $C_{12}$-$C_{22}$alkatrienoyl or phenyl which is substitute; and (c) water.

2. A composition according to claim 1, wherein said composition further includes up to 5% by weight of a water soluble or water dispersible viscosity modifying agent.

3. A composition according to claim 1, wherein said composition further includes up to 25% by weight of a frost protective agent.

* * * * *